US008747862B2

(12) United States Patent
Smith et al.

(10) Patent No.: US 8,747,862 B2
(45) Date of Patent: Jun. 10, 2014

(54) PATHOGENIC WEST AFRICAN HUMAN IMMUNODEFICIENCY VIRUS TYPE 2 (HIV-2) GROUP F ISOLATE

(75) Inventors: Stephen M. Smith, Essex Falls, NJ (US); Preston A. Marx, Covington, LA (US)

(73) Assignee: Tulane University Health Sciences Center, New Orleans, LA (US)

( * ) Notice: Subject to any disclaimer, the term of this patent is extended or adjusted under 35 U.S.C. 154(b) by 356 days.

(21) Appl. No.: 13/129,282

(22) PCT Filed: Nov. 13, 2009

(86) PCT No.: PCT/US2009/064349
§ 371 (c)(1),
(2), (4) Date: Jan. 17, 2012

(87) PCT Pub. No.: WO2010/056966
PCT Pub. Date: May 20, 2010

(65) Prior Publication Data
US 2012/0107909 A1 May 3, 2012

Related U.S. Application Data

(60) Provisional application No. 61/163,190, filed on Mar. 25, 2009, provisional application No. 61/114,807, filed on Nov. 14, 2008.

(51) Int. Cl.
*A61K 39/21* (2006.01)
(52) U.S. Cl.
USPC .................................................. 424/208.1
(58) Field of Classification Search
None
See application file for complete search history.

(56) References Cited

U.S. PATENT DOCUMENTS

| 4,816,567 | A | 3/1989 | Cabilly et al. |
| 6,020,123 | A | 2/2000 | Sonigo et al. |

OTHER PUBLICATIONS

Fitch, W. M., May 2000, Homology: a personal view on some of the problems, TIG 16(5):227-231.*
Gerhardt, M., et al., Jul. 2005, In-depth, longitudinal analysis of viral quasispecies from an individual triply infected with late-stage human immunodeficiency virus type 1, using a multiple PCR primer approach, J. Virol. 79(13):8249-8261.*
Duarte, E. A., et al., 1994, RNA virus quasispecies: significance for viral disease and epidemiology, Infect. Agents Dis. 3:201-214.*
Charpentier, C., et al., Mar. 2006, Extensive recombination among human immunodeficiency virus type 1 quasispecies makes an important contribution to viral diversity in individual patients, J. Virol. 80(5):2472-2482.*
Chen et al., "Genetic Characterization of New West African Simian Immunodeficiency Virus SIVsm: Geographic Clustering of Household-Derived SIV Strains with Human Immunodeficiency Virus Type 2 Subtypes and Genetically Diverse Viruses from a Single Feral Sooty Mangabey Troop," *J. Virol.* 70(6):3617-3627 (1996).
Chen et al., "Human Immunodeficiency Virus Type 2 (HIV-2) Seroprevalence and Characterization of a Distinct HIV-2 Genetic Subtype from the Natural Range of Simian Immunodeficiency Virus-Infected Sooty Mangabeys," *J. Virol.* 71(5):3953-3960 (1997).
Clackson et al., "Making antibody fragments using phage display libraries," *Nature* 352:624-628 (1991).
Damond et al., "Identification of a highly divergent HIV type 2 and proposal for a change in HIV type 2 classification," *AIDS Res. Hum. Retroviruses* 20(6):666-672 (2004).
Department of Health and Human Services, Panel on Antiretroviral guidelines for Adults and Adolescents. "Guidelines for the use of antiretroviral agents in HIV-1-infected adults and adolescents." Jan. 29, 2008; 1-127. [online] http://www.aidsinfo.nih.gov/Contentfiles/AdultandAdolescentGL.pdf. Accessed Oct. 23, 2008.
Department of Health and Human Services Panel on Guidelines for the Prevention and Treatment of Opportunistic Infections in HIV-Infected Adults and Adolescents. "Guidelines for the Prevention and Treatment of Opportunistic Infections in HIV-Infected Adults and Adolescents," Jun. 18, 2008; 1-302 [online] http://www.aidsinfo.nih.gov/Contentfiles/Adult_OI.pdf. Accessed Oct. 23, 2008.
Gao et al., "Genetic Diversity of Human Immunodeficiency Virus Type 2: Evidence for Distinct Sequence Subtypes with Differences in Virus Biology," *J. Virol.* 68(11):7433-7447 (Nov. 1994).
Gorelick et al., "Nucleocapsid protein zinc-finger mutants of simian immunodeficiency virus strain mne produce virions that are replication defective in vitro and in vivo," *Virol.* 253(2):259-270 (1999).
Gottlieb et al., "Differences in proviral DNA load between HIV-1-infected and HIV-2-infected patients," *AIDS* 22(11):1379-1380 (2008).
Hamel et al., "Twenty years of prospective molecular epidemiology in Senegal: changes in HIV diversity," *AIDS Res. Hum. Retroviruses* 23:1189-1196 (2007).
International Patent Application No. PCT/US2009/064349: International Search Report and Written Opinion, dated Sep. 13, 2010.
Kimata et al., "A Lymph Node-Derived Cytopathic Simian Immunodeficiency Virus Mne Variant Replicates in Nonstimulated Peripheral Blood Mononuclear Cells," *J. Virol.* 72(1):245-256 (Jan. 1998).
Kohler and Milstein "Continuous cultures of fused cells secreting antibody of predefined specificity," *Nature* 256:495-499 (1975).
Laure et al., "Detection of HIV1 DNA in infants and children by means of the polymerase chain reaction," *Lancet* 332(8610):538-541 (1988).
Marks et al., "By-passing immunization. Human antibodies from V-gene libraries displayed on phage," *J. Mol Biol.* 222(3):581-597 (1991).

(Continued)

*Primary Examiner* — Jeffrey S. Parkin
(74) *Attorney, Agent, or Firm* — Finnegan, Henderson, Farabow, Garrett & Dunner, LLP

(57) ABSTRACT

The claimed invention is directed toward an HIV-2 isolate designated NWK08F, including variants, and isolated proteins and nucleotides obtained from said isolates.

2 Claims, 2 Drawing Sheets

(56) References Cited

OTHER PUBLICATIONS

Marlink et al., "Reduced rate of disease development after HIV-2 infection as compared to HIV-1," *Science* 265(5178):1587-1590 (1994).

Novembre et al., "Multiple Viral Determinants Contribute to Pathogenicity of the Acutely Lethal Simian Immunodeficiency Virus SIVsmmPBj Variant," *J. Virol.* 67(5):2466-2474 (May 1993).

Popper et al., "Low Plasma Human Immunodeficiency Virus Type 2 Viral Load Is Independent of Proviral Load: Low Virus Production In Vivo," *J. Virol.* 74(3):1554-1557 (2000).

Posada et al., "Selecting the Best-Fit Model of Nucleotide Substitution," *Syst. Biol.* 50(4):580-601 (2001).

Rychert et al., "Genetic Analysis of Simian Immunodeficiency Virus Expressed in Milk and Selectively Transmitted Through Breastfeeding," *J. Virol.* 80(8):3721-3731 (2006).

Van Der Loeff et al., "Sixteen Years of HIV Surveillance in a West African Research Clinic Reveals Divergent Epidemic Trends of HIV-1 and HIV-2," *Int. J Epidomiol.* 35:1322-28 (2006).

\* cited by examiner

FIG. 1

PATHOGENIC WEST AFRICAN HUMAN IMMUNODEFICIENCY VIRUS TYPE 2 (HIV-2) GROUP F ISOLATE

This is a U.S. National Phase Application of PCT/US2009/064349, filed Nov. 13, 2009, which claims the benefit of priority to U.S. Provisional Patent Application No. 61/114,807, filed Nov. 14, 2008, and to U.S. Provisional Patent Application No. 61/163,190, filed Mar. 25, 2009, all of which are incorporated herein by reference in their entireties.

DESCRIPTION OF THE INVENTION

Substantial progress has been made in our understanding of acquired immune deficiency syndrome (AIDS). The principal causative agent of AIDS is human immunodeficiency virus (HIV), a non-transforming retrovirus with a tropism for CD4 T-helper cells. AIDS is characterized by a progressive depletion of the CD4 T cell population with a concomitant increasing susceptibility to the opportunistic infections that are characteristic of the disease. Epidemiological studies indicate that HIV-1 is the etiological agent responsible for the majority of AIDS cases and these infections are widely spread throughout the world.

A second type of HIV, HIV-2, has been isolated from patients in West Africa, but has not appreciably spread beyond this area. The incidence of HIV-2 infection has declined over the last 16-20 years (Hamel et al., *AIDS Res Hum Retroviruses* 23:1189-96 (2007); Van der Loeff et al., *Int J Epidemiol* 35:1322-28 (2006)). There are at least 8 known subtypes of HIV-2, referred to as subtypes A-H. The majority of human HIV-2 infections are caused by subtypes A and B, which are known as the epidemic subtypes. Only a small percentage of individuals infected with HIV-2 subtypes A and B develop the immunodeficiency characteristic of AIDS (Marlink et al., *Science* 265:1587-90 (1994). Infections with the non-epidemic HIV-2 subtypes C-G are generally known only as single person infections, and have not been shown to lead to immunodeficiency (Gao et al., *J Virol* 68:7433-47 (1994); Chen et al., *J Virol* 71:2953-60 (1997)). There is also only one known case of a person infected with HIV-2 subtype H, and this virus caused immunodeficiency in the infected man from the Ivory Coast (Damond et al., *AIDS Res Hum Retroviruses* 20:666-72 (2004)).

HIV-2 subtype F was discovered 16 years ago in an individual from Sierra Leone (Chen et al., *J Virol* 71:2953-60 (1997)). Despite repeated attempts, live virus was never isolated from the infected patient and the patient remained healthy during the time of observation.

We have now identified a new strain of HIV-2. It is accordingly a primary object of the invention to provide a novel strain of Subtype F HIV-2, nucleic acids and polypeptides derived from this virus, and methods of detecting the presence of this novel virus in patients and cell culture.

In one embodiment, the invention provides an isolated HIV-2 virus comprising the virus deposited at the American Type Culture Collection ("ATCC") (ATCC, 10801 University Boulevard. Manassas, Va. 20110-2209) as HIV-2NWK08F. In some embodiments, this HIV-2 virus comprises the nucleotide sequence of SEQ ID NO:1 or SEQ ID NO:3. In an additional embodiment, the HIV-2 virus is a variant of HIV-2NWK08F, wherein the variant comprises a nucleotide sequence with 95% homology to SEQ ID NO:1 or SEQ ID NO:3.

In one embodiment, the invention provides a nucleic acid comprising a nucleotide sequence of SEQ ID NO:1 or SEQ ID NO:4, or fragments thereof. This nucleic acid may comprise at least 6 contiguous nucleotides of SEQ ID NO:1 or SEQ ID NO:4. In some embodiments, the nucleic acid contains a detectable label.

In other embodiments, the invention provides a polypeptide comprising an amino acid sequence of SEQ ID NO:2, SEQ ID NO:3, SEQ ID NO:5, or SEQ ID NO:6, or fragments thereof. This polypeptide may comprise at least 6 contiguous amino acids of SEQ ID NO:2, SEQ ID NO:3, SEQ ID NO:5, or SEQ ID NO:6. In particular embodiments the polypeptide encodes the Env, Pol, Gag, or Nef protein of HIV-2NWK08F.

In another embodiment, the invention provides an antibody that specifically binds to a polypeptide derived from the HIV-2NWK08F virus. In some embodiments, the antibody specifically binds to an Env, Pol, Gag, or Nef polypeptide of HIV-2NWK08F, but does not bind to Env polypeptides from other HIV-1 or HIV-2 virus strains.

In another embodiment, the antibody specifically binds to an Env, Pol, Gag, or Nef polypeptide of HIV-2 subtype F, but does not bind to Env polypeptides from other HIV-1 or HIV-2 virus strains or subtypes.

The invention also provides compositions and methods for detecting HIV-2NWK08F nucleic acids and polypeptides. In one embodiment, the invention provides a composition for detecting HIV-2NWK08F nucleic acids comprising at least 6 contiguous nucleotides of SEQ ID NO:1 or SEQ ID NO:4. In another embodiments, the invention provides a method for detecting HIV-2NWK08F nucleic acids in a biological sample comprising (a) contacting the biological sample with a composition comprising a nucleotide sequence of HIV-2NWK08F; and (b) detecting the hybridization of the HIV-2NWK08F nucleotide sequence to the nucleic acid of the biological sample.

In some embodiments, the methods for detecting HIV-2NWK08F nucleic acids involve the amplification of HIV-2NWK08F nucleic acids prior to or during the detection step.

In one embodiment, the invention provides a method of detecting HIV-2NWK08F nucleic acids in a biological sample comprising (a) contacting the biological sample with primers derived from HIV-2NWK08F capable of amplifying an HIV-2NWK08F genome;

(b) amplifying the HIV-2NWK08F nucleic acid; and (c) detecting the presence of amplified HIV-2NWK08F nucleic acid.

In another embodiment, the invention provides a composition for detecting HIV-2NWK08F polypeptides comprising an antibody specific for those polypeptides. In an exemplary embodiment, the invention provides a method for detecting HIV-2NWK08F polypeptides in a biological sample comprising (a) contacting the biological sample with a composition comprising at least one anti-HIV-2NWK08F antibody; and (b) detecting an immunological complex formed between the polypeptide and the antibody used.

The invention also provides compositions and methods of detecting antibodies specific for HIV-2NWK08F. In one embodiment, the invention provides compositions for detecting antibodies specific for HIV-2NWK08F comprising at least 6 contiguous amino acids of SEQ ID NO:2, SEQ ID NO:3, SEQ ID NO:5, or SEQ ID NO:6. In another embodiment, the invention provides a method for detecting antibodies against HIV-2NWK08F virus in a biological sample comprising:

(a) contacting the biological sample with a composition comprising at least one antigen of the HIV-2NWK08F virus; and (b) detecting an immunological complex formed between the anti-HIV-2NWK08F antibodies and the antigen used.

In another embodiment, the invention provides a method for the preparation of hybridomas which produce monoclonal antibodies specific for the HIV-2NWK08F Env of Gag polypeptide, comprising the following the steps:

(a) immunizing a mammal with a polypeptide from the HIV-2NWK08F Env or Gag polypeptide or immunogenic fragment thereof;

(b) isolating immunized splenocytes from said mammal;

(c) fusing the immunized splenocytes with a myeloma cell line to produce hybridomas;

(d) selecting for the hybridomas by culturing in selective media;

(e) clonally expanding the hybridomas in appropriate culture media; and, (f) identifying and characterizing those hybridomas that produce monoclonal antibodies specific for HIV-2NWK08F Env, Pol, Gag, or Nef polypeptide.

In yet another embodiment, the invention provides methods of treating patients infected with HIV-2NWK08F by administering anti-viral drugs.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 1 is a phylogenetic tree showing the relationship between HIV-2NWK08F env gene sequences to other HIV and SIV strains.

BRIEF DESCRIPTION OF THE SEQUENCES

Figure 2:
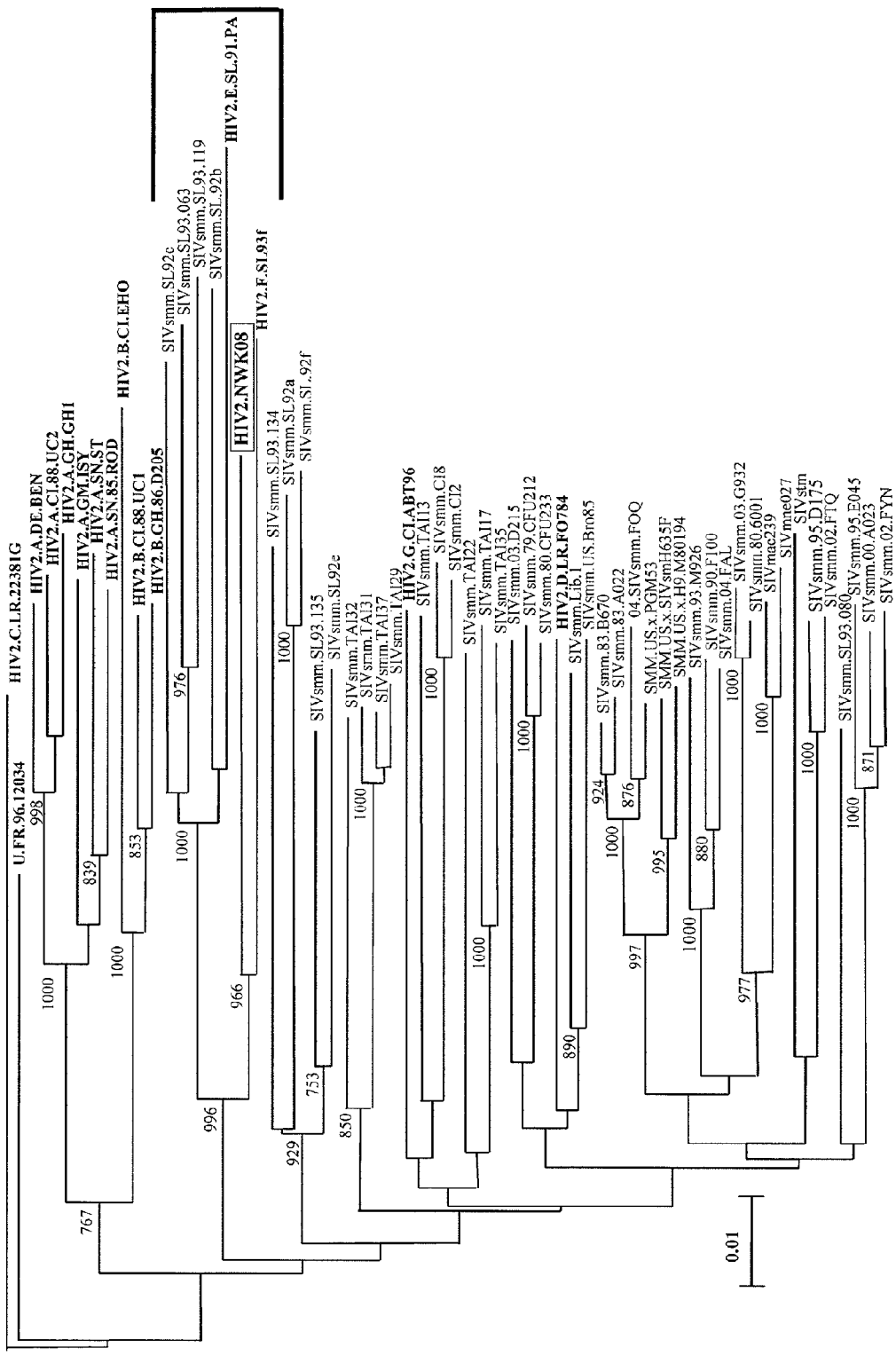
FIG. 2 is a phylogenetic tree showing the relationship between HIV-2NWK08F gag gene sequences to other HIV and SIV strains.

The instant application contains a Sequence Listing which has been submitted via EFS-Web and is hereby incorporated by reference in its entirety. Said ASCII copy, created on Nov. 12, 2009, is named 09932000.txt, and is 25,235 bytes in size.

SEQ ID NO:1 is a partial nucleotide sequence of the env and nef genes of HIV-2NWK08F.

SEQ ID NO:2 is a partial amino acid sequence of the Env polypeptide of HIV-2NWK08F.

SEQ ID NO:3 is a partial amino acid sequence of the Nef polypeptide of HIV-2NWK08F.

SEQ ID NO:4 is the full nucleotide sequence of gag gene of HIV-2NWK08F and a partial nucleotide sequence of the 5'-LTR and the pol gene of HIV-2NWK08F.

SEQ ID NO:5 is the full amino acid sequence of the Gag polypeptide of HIV-2NWK08F.

SEQ ID NO:6 is a partial amino acid sequence of the Nef polypeptide of HIV-2NWK08F.

SEQ ID NOs:7-20 are primers derived from the env/nef genes of HIV-2 subtype F virus.

SEQ ID NOs:21-36 are primers derived from the gag/pol gene of HIV-2 subtype F virus.

SEQ ID NOs:37-40 are primers derived from the env gene of HIV-2 subtype F virus.

SEQ ID NOs:41-44 are primers derived from the gag gene of HIV-2 subtype F virus.

SEQ ID NOs:45 and 46 are primers derived from the env gene of HIV-2NWK08F for use in a real time PCR assay for HIV-2NWK08F viral load.

SEQ ID NO:47 is a probe derived from the env gene of HIV-2NWK08F for use in detection of the PCR products in a real time PCR assay for HIV-2NWK08F viral load.

DESCRIPTION OF THE EMBODIMENTS

The invention is based, in part, on the discovery of a novel strain of HIV-2 in a patient in Newark, N.J. The invention is further based, in part, on the isolation of an HIV-2 virus, referred to as HIV-2NWK08F, from the patient. The invention is also based, in part, on the nucleic acid sequence of this virus, and in particular, the nucleic acid sequence of the genes encoding the Gag and Env polypeptides of this virus.

Patient X, a 68 year old man, moved from his homeland of Sierra Leone to New Jersey in 2007. During the immigration process, he tested positive in a general screen for antibodies to HIV. Upon further investigation, Patient X repeatedly tested positive for antibodies in an assay that detected antibodies against either HIV-1 or HIV-2. However, the patient's blood tested negative for HIV-1 by Western blot and PCR assays. His HIV-1 viral load was below the lower limit of the assay (a quantitative RT-PCR assay from LabCorp). Interestingly, the patient tested positive for HIV-2 antibodies, but a PCR assay for HIV-2 proviral DNA was negative, indicating that the patient may have been infected with an unidentified strain of HIV-2.

Patient X had a CD4 T-cell count of 338 cells/μl and a CD4:CD8 ratio of 0.52. These results are indicative of CD4 T-cell lymphopenia. The combination of the results from the HIV testing and the patient's reduced CD4 T-cell count suggested that Patient X was actively infected with an unrecognized strain of HIV-2.

Co-culture of Patient X's peripheral blood mononuclear cells (PBMCs) with PHA-stimulated normal donor PMBCs or CEM-X-174 cells resulted in viral isolation. Portions of the env and gag genes of the provirus produced by these cells were successfully amplified by PCR with primers derived from an HIV-2 subtype F strain (Chen et al., *J Virol* 71:3953-3960 (1997), incorporated by reference herein). The amplified regions were sequenced and a real-time PCR protocol was developed with primers derived from the env gene of the new virus to quantify viral load. Two recent studies of HIV-2 infected individuals found the median proviral load to be ~300 copies per $10^6$ PBMC (Gottleib et al., AIDS 22:1379-80 (2008); Popper et al., *J Virol* 74:1554-57 (2000)). In contrast, Patient X had a proviral load of 6,100 copies per $10^6$ PBMC.

The sequenced regions of the new virus were subjected to phylogenetic comparisons to existing HIV strains (Posada, et al., *Syst Biol* 50:580-601 (2001); Swofford, PAUP*. Phylogenetic analysis using parsimony (*and other methods), version 4. Sinauer Associates, Sunderland, Mass. (1999)). HIV-2NWK08F clustered significantly with four other viruses, all from Sierra Leone. Two of the viruses (strains of HIV-2 subtypes E and F) have not been known to cause immune suppression, nor have they been shown to be transmitted from person to person. The other 2 viruses were simian immunodeficiency viruses (SIVs) found in sooty mangabey monkeys in Sierra Leone, documenting transmission from monkey to humans in the area. It is unknown how Patient X acquired the virus. Since he denies exposure to monkeys and has not received blood or blood product transfusions, he most likely contracted the virus from another person.

Accordingly, the invention provides a new strain of HIV-2 virus, the nucleotide sequence of the virus, viral proteins and fragments thereof, methods of detecting HIV-2 virus infection, and methods of treating a patient infected with HIV-2.

Viruses

The invention provides an isolated virus, known as HIV-2NWK08F. HIV-2NWK08F was deposited with the American Type Culture Collection ("ATCC") (ATCC, 10801 University Boulevard. Manassas, Va. 20110-2209) according to the provisions of the Budapest Treaty. All restrictions on the availability to the public of the above ATCC deposit will be irrevocably removed upon the granting of a patent on this application. In another embodiment, the invention provides variants of this virus comprising a nucleotide sequence of SEQ ID NO:1 or SEQ ID NO:3 or a sequence substantially homologous to SEQ ID NO:1 or SEQ ID NO:3, i.e., at least about 85%, about 90% or about 95% homologous at the nucleotide level. In yet another embodiment, the invention provides variants of the virus that encodes polypeptides comprising an amino acid sequence of SEQ ID NO:2 or SEQ ID NO:4 a sequence substantially homologous to SEQ ID NO:2 or SEQ ID NO:4, i.e., at least about 85%, about 90% or about 95% homologous at the amino acid level. The invention also provides cells or mammals (including humans) infected with an isolated HIV-2NWK08F virus or variant.

The invention also relates to HIV-2 variants characterized by the nucleotide sequences of the HIV-2NWK08F virus deposited at the ATCC, as well as related variants that comprise a nucleotide sequence that is substantially homologous to the sequences of the virus deposited at the ATCC as HIV-2NWK08F, i.e., at least about 85%, 90% or 95% homologous at the nucleotide level. The sequences of HIV-2NWK08F and its variants disclosed herein characterize a new HIV-2 virus that is part of a subclass of HIV-2 viruses, currently known to be found primarily in Sierra Leone.

"Purified" or "isolated" HIV isolate refers to a preparation of HIV virus particles which has been isolated from the cellular constituents with which the virus is normally associated, and from other types of viruses which may be present in the infected tissue. The techniques for isolating viruses are known to those of skill in the art, and include, for example, centrifugation and affinity chromatography.

An HIV "particle" is an entire virion, as well as particles which are intermediates in virion formation. HIV particles generally have one or more HIV proteins associated with the HIV nucleic acid.

Nucleic Acids

The invention provides a nucleic acid comprising a nucleotide sequence of HIV-2NWK08F. In some embodiments, the nucleic acid is RNA. In other embodiments, the nucleic acid is DNA. In particular embodiments, the nucleic acid is isolated viral RNA or proviral DNA. In other embodiments, the nucleic acid is a cDNA molecule. In other embodiments, the nucleic acid is an oligonucleotide. The nucleic acid may be naturally-occurring, non-naturally occurring, recombinantly produced, or synthetic.

The nucleic acid molecules of the present invention may be used, e.g., (1) to produce HIV-2NWK08F polypeptides; (2) as probes in nucleic acid hybridization assays; (3) as primers for reactions involving the synthesis of HIV-2NWK08F nucleic acid; (4) as binding partners for separating HIV-2NWK08F viral nucleic acid from other constituents which may be present; (5) as a component of a partial or complete HIV-2NWK08F virion; and (6) as anti-sense nucleic acid for preventing the transcription or translation of viral nucleic acid.

In some embodiments, the nucleic acid comprises the entire viral genome. In other embodiments, the invention provides a nucleic acid comprising sequences that encode the Env, Nef, Gag, or Pol protein of HIV-2NWK08F. In particular embodiments, the invention provides a nucleic acid comprising all or a portion of SEQ ID NO:1 or SEQ ID NO:4 or their complements. In particular embodiments, the invention provides a nucleic acid that encodes all or a portion of the amino acid sequence of SEQ ID NO:2, SEQ ID NO:3, SEQ ID NO:5, or SEQ ID NO:6.

TABLE 1

HIV-2NWK08F Sequences

Env/Nef Nucleotide Sequence: SEQ ID NO: 1
TACCTTCATGTGGACAAATTGCAGAGGAGAATTTTTATATTGTAAAATGAATTGGTTCCT
AAATTGGGTAGAAGACAGAAATATAACTCATGGAAGATGGAGTACTCAAAAACCAGCAGA
GAAACAGAAGAGGAACTATGTGCCTTGCCACATAAGGCAAATCATAAATACTTGGCACAA
AGTAGGGAAAAATGTGTACCTGCCTCCAAGAGAAGGTAATCTAACGTGTAACTCATCAGT
AACAAGCATAATTGCAAACATAGACTGGACAAGCGACAATGAAACTAATATCACCATGAG
TGCAGAAGTGGCAGAACTGTATCGATTAGAGTTGGGTGACTATAAATTAGTAGAGATAAC
ACCAATTGGCTTGGCCCCAACAGAAGTAAAAAGATATTCCTCAGCAACACCGAGGAATAA
GAGAGGGGTCTTTGTGCTAGGGTTCTTGGGATTTCTCGCAACGGCAGGTTCTGCAATGGG
CGCAGCGTCGCTGACGCTGACAGCTCAGTCTCGGACTTTACTGGCTGGGATAGTGCAGCA
ACAGCAGCAGCTGTTGGATGCAGTCAAGAGACAACAAGAATTGTTGCGATTGACAGTCTG
GGGGACTAAAAACCTCCAGACACGCGTCACTGCCATCGAGAAATACCTAAAGGATCAGGC
ACAGCTAAATTCATGGGGGTGTGCATTTAGACAGGTCTGCCATACTACTGTACCATGGCC
AAATGACACATTGCAACCAAATTGGGACAACATGACTTGGCAAGAGTGGGAAAGGAAAGT
AGACTTTCTCACAGAAAACATCACAGAACTCTTGGAGCAGGCACAGATTCAACAAGAAAA
AAATATGTATGAACTACAAAAATTGAACAGCTGGGATGTGTTTGGCAATTGGTTTGACCT
CAGCTCCTGGATCACCTACATACAGTATGGAGTATACTTAGTAGTAGGAGTAATAGGGCT
TAGAATAAGTATATATATAGTACAGATGCTATTGAGGCTTAGAAAGGGCTATAGGCCCGT
GTTCTCTTCCCCACCCTCTTATCGCCAGCAGATCCATATCCGACGGGACCAGGAACTGCC
AGACGGAGAAGACAGAGAAGAAGACGGTGGAGAAAAAGGTGGCAACAGATCCTGGCCCTG
GCAGATAGAGTACATTCATTTCCTGATCCGCCAGTTGATTCGCCTCTTGACTTGGCTATA
CAGCAATTGCAGAGACTTAATATACAAGAGCTTCCAGACCCTCCACCAGCTGACCAGTGC
AGCAGCAACAGCAACTAGAGACTTTATCAGAACAGAAGCCAGTTACATCAGCTATGGGTG
GCAATACTTCCTCGAAGCCCTCCAAGCGGCAATGCAGACTGCGGGAGAGACTCTTGCAAG
CGCGGGGGGAGAATTATGGGCAACTCTGGGAAGGATT (SEQ ID NO: 1)

Env Amino Acid Sequence: Encoded by nucleotides 8-1417 of SEQ ID NO: 1
MWTNCRGEFLYCKMNWFLNWVEDRNITHGRWSTQKPAEKQKRNYVPCHIRQIINTWHKVGKNVYLPPREG
NLTCNSSVTSIIANIDWTSDNETNITMSAEVAELYRLELGDYKLVEITPIGLAPTEVKRYSSATPRNKRG

TABLE 1 -continued

HIV-2NWK08F Sequences

VFVLGFLGFLATAGSAMGAASLTLTAQSRTLLAGIVQQQQQLLDAVKRQQELLRLTVWGTKNLQTRVTAI
EKYLKDQAQLNSWGCAFRQVCHTTVPWPNDTLQPNWDNMTWQEWERKVDFLTENITELLEQAQIQQEKNM
YELQKLNSWDVFGNWFDLSSWITYIQYGVYLVVGVIGLRISIYIVQMLLRLRKGYRPVFSSPPSYRQQIH
IRRDQELPDGEDREEDGGEKGGNRSWPWQIEYIHFLIRQLIRLLTWLYSNCRDLIYKSFQTLHQLTSAAA
TATRDFIRTEASYISYGWQYFLEALQAAMQTAGETLASAGGELWATLGRI(SEQ ID NO: 2)

Nef Amino Acid Sequence: Encoded by nucleotides 1314-1417 of SEQ ID NO: 1
MGGNTSSKPSKRQCRLRERLLQARGENYGQLWEG (SEQ ID NO: 3)

5' LTR/Gag/Pol Nucleotide Sequence: SEQ ID NO: 4
5' LTR: nucleotides 1-827 of SEQ ID NO: 4
Gag polypeptide: nucleotides 1046-2560 of SEQ ID NO: 4
Env polypeptide (partial): nucleotides 2218-2263 of SEQ ID NO: 4
TGGAAGGGATGTTTTACAGTGAGAGGAGGCATAGAATATTAGACACATAC
TTAGAAAAGGAGGAAGGAATAGTTCCAGATTGGCAGAATTATACACGGGG
ACCAGGTATTAGATATCCAAATACTTTGGCTGGCTATGGCAGCTGGAAC
CAGTGGACGTCTCAGAAGAAAATGATGAGACAAATTGTCTGGTCCATCCA
GCGCAGACAAGTCAGTGGGACGACCCATGGGGGAAACTCTAGTATGGAG
ATTTAATTCTGCATTGGCTTACACCTATGAGGCTTACATTAGACATCCAG
AAGAGTTTGGTTGGAAGTGAGGCCTGTCAGAGGAAGAGGTTAAGCAGAGA
CTGGCTGACAGGAAGAAGCCAACCACAAAGTAAGATGGCGGACAGAAAGG
AAACTAGCTGAGATAGCAGGGACTTTCCAACAAGGGGACGGGCAATGGGT
GGAGACTGGGCGGGGGGTATGGGAACGCCCCATTTTACTCTGTATAAATG
TACCCGCTTACTGCTCTGTAATCAGTCGCTCTGCGGAGAGGCTGCCAGGT
AGAGCCCCGAGTGGATCCCTGGTAGCACTAGCAGGAGAGCCTGGGTGTTC
CCTGCTAGACTCTCACTGGTGCTTGGCCAGTACCAGGCAGACGGCTCCAC
GCTTGCTTGCTTGACTCTCAATAAAGCTGCCATTTAGAAGCAAGTCAGCG
TGTGTTCCCATCTCTTCTAGTCGCCGCCTGGTCATTCGGTGTCCTGGCTC
GAGGTCTCGGTATCAAGTCCCTGGAACTGTCAGAACCCTCTCACTAAGGG
GCAACCCTGAGTGAAAAATCTCTGGCAGTTTGGCGCCCGAACAGGGACAT
GAGAGACCTGAGAAAGCACACGGCTGAGTGAAGGCAGCAAGGGCGGCAGA
AACCAACCGCGACGGAGGAAGACCCGGTGCCAGAGGGCTGAGCGGGACGT
GAAGGTAAGAGAGGCCTTCGGGACAGATAGTCCAAAGTTTGTGTAGCTAT
AGAGCTGTTTCCCTACCCTCAAGGAGGGTAGAAGTATAGCGGGAGATGGG
CGCGAGACACTCCGTCTTGTCAGGGAAAAAAGCAGATGAATTAGAAAAAG
TTAGGTTACGGCCCGGCGGAAAGAAAAAGTATATGTTAAAGCATATAATA
TGGGCAGCAAAAGAATTGGACAGATTCGGATTGGCAGAAGACCTGTTGGA
AAACAAACAAGGATGTCAAAGAATATTAGAAGTTTTAACCCCATTAATGC
CAACAGGCTCAGAAAATTTAAAGAGTTTGTATAATACTGTCTGCGTAGTT
TGGTGTTTGCACGCAGAAGAGAAAGTGAAACACACAGAGGAAGCAAAGCA
GTTGGTACAGAGACATCTAGTGGCAGAAACTAAAACTGCAGAAAAAATAC
CAGCAAAAAGTAGACCAACAGCTCCACCTAGTGGAGGAAATTATCCAGTG
CAGCAAGTAGGTGGAAATTATGTCCACTTACCATTAAGCCCCAGAACTTT
AAATGCCTGGGTAAAATTAGTAGAGGAAAAGAAATTTGGAGCAGAAGTAG
TGCCAGGCTTTCAGGCACTGTCAGAAGGCTGCACACCTTATGATATTAAT
CAGATGCTAAATTGTGTAGGGGAACATCAAGCGGCTATGCAAATAATTAG
AGAAATTATCAATGAGGAAGCAGCAGACTGGGACGCACAGCATCCAAGGC
AGCTACCGGCACCTCCGGGGCTGCGCGACCCGTCAGGGTCAGATATAGCA
GGAACCACCAGTACTGTAGAAGAGCAAATAGAGTGGATGTATAGACAAGG
AAATCCTGTCCCAGTAGGACAAATTTACAGGAGATGATTCAGCTAGGAT
TACAAAAATGTGTAAGAATGTACAATCCCACTAACATTCTAGACGTAAAG
CAAGGTCCAAAAGAGCCATTCCAAGTTTATGTAGACAGGTTCTACAAAAG
TTTGAGAGCAGAACAAACAGACCCAGCAGTGAAGAATTGGATGACCCAAA
CACTGCTGATCCAAAATGCCAACCCTGATTGCAAACTAGTATTAAAAGGA
TTGGGAATGAATCCCACCTTAGAAGAAATGTTAACAGCTTGTCAGGGAGT
GGGAGGTCCTGGACAAAAGGCTAGGTTAATGGCCGAGGCAATGAAGGAAG
CCTTTAATGGCTCCTTCGCGGCCGTGCAGATGAGAGGGAAACAACAGAAG
GGGGCATCAACTATTAGATGCTTTAATTGTGGGAAACCAGGCCACACTGC
CAGAAATTGCAGGGCACCAAGAAGAAAGGGGTGCTGGAAATGTGGAGAGG
AAGGACACATGCAAGCAAACTGCCCAAACCAACGGGCGGGTTTTTTAGGG
TTAGGACCATGGGGAAGAAGCCTCGCAACTTCCCCATGAGACAGATGCC
AGAGGGACTGACCCCATCAGCCCCTCCGGACCCAGCAGCAGAAATGCTCG
AGGAGTATATGCAGAAGGGGAAAAGTCAGAGGGAGCAGAGGGAGAGACCT
TACAAAGAGGTGACGGAGGACTTGCTGCACCTCAGTTCTCTCTTTGGAAA
AGACCAGTAGTCACAGCATATATAGAGGATCAGCCAGTACAGGTACTGCT
AGATACAGGAGCTGATGACTCTATAGTGGCAGGGATAGAATTAGGACTTA
ATTACAAGCCAAA (SEQ ID NO: 4 )

Gag Amino Acid Sequence: SEQ ID NO: 5
MGARHSVLSGKKADELEKVRLRPGGKKKYMLKHIIWAAKELDRFGLAEDLLENKQGCQRILEVLTPLMPT
GSENLKSLYNTVCVVWCLHAEEKVKHTEEAKQLVQRHLVAETKTAEKIPAKSRPTAPPSGGNYPVQQVGG
NYVHLPLSPRTLNAWVKLVEEKKFGAEVVPGFQALSEGCTPYDINQMLNCVGEHQAAMQIIREIINEEAA
DWDAQHPRQLPAPPGLRDPSGSDIAGTTSTVEEQIEWMYRQGNPVPVGQIYRRWIQLGLQKCVRMYNPTN
ILDVKQGPKEPFQVYVDRFYKSLRAEQTDPAVKNWMTQTLLIQNANPDCKLVLKGLGMNPTLEEMLTACQ

TABLE 1 -continued

HIV-2NWK08F Sequences

GVGGPGQKARLMAEAMKEAFNGSFAAVQMRGKQQKGASTIRCFNCGKPGHTARNCRAPRRKGCWKCGEEG
HMQANCPNQRAGFLGLGPWGKKPRNFPMRQMPEGLTPSAPPDPAAEMLEEYMQKGKSQREQRERPYREVT
EDLLHLSSLFGKDQ (SEQ ID NO: 5)

Pol Amino Acid Sequenc: SEQ ID NO: 6
MWETRPHCQKLQGTKKKGVLEMWRGRTHASKLPKPTGGFFRVRTMGKEASQLPHETDARGTDPISPSGPS
SRNARGVYAEGEKSEGAEGETLQRGDGGLAAPQFSLWKRPVVTAYIEDQPVQVLLDTGADDSIVAGIELG
LNYKP (SEQ ID NO: 6)

In some embodiments, the invention provides a nucleic acid that hybridizes under stringent conditions to the nucleotide sequence of SEQ ID NO:1 or SEQ ID NO:4. In certain embodiments, stringent conditions include, but are not limited to (1) wash in aqueous prehybridization buffer (6×SSC, 5×Denhardt's reagent, 0.5% SDS) at 68° C.; (2) hybridization of the probe in aqueous hybridization buffer (6×SSC, 5×Denhardt's reagent, 0.5% SDS, 1 µg/ml poly(A), 100 µg/ml salmon sperm DNA) at 68° C.; and (3) wash in 2×SSC, 0.5% SDS at room temperature. Alternatively, stringent conditions include, but are not limited to (1) wash in formamide prehybridization buffer (6×SSC, 5×Denhardt's reagent, 0.5% SDS, 50% formamide) at 42° C.; (2) hybridization of the probe in formamide hybridization buffer (6×SSC, 5×Denhardt's reagent, 0.5% SDS, 50% formamide, 1 µg/ml poly(A), 100 µg/ml salmon sperm DNA) at 42° C.; and (3) wash in 2×SSC, 0.5% SDS at room temperature. Additional variations on these stringent conditions are know to one of skill the art and may be found, for example, in Chapter 6 of Sambrook & Russell, *Molecular Cloning: A Laboratory Manual*, CSHL Press, 2001, which is incorporated by reference herein. In exemplary embodiments, the invention provides a nucleic acid that is at least about 80%, 85%, 90%, 95%, 96%, 97%, 98%, or 99% identical to the nucleotide sequence of SEQ ID NO:1 or SEQ ID NO:4, or fragments thereof.

In some embodiments, the nucleic acid that hybridizes under stringent conditions is a probe or a primer. The probe or the primer maybe used to detect the presence of HIV-2NWK08F or other HIV strains in a biological sample. Exemplary primers are set forth below in Tables 2 and 3.

TABLE 2

HIV-2NWK08F Env-Nef Primers

| | Primer | Primer Sequence | PCR Fragment Size |
|---|---|---|---|
| 1 | Outer Forward | 5'-GGA GGA GGA GAT CCG GAA GT-3' SEQ ID NO: 7 | 492 bp |
| | Outer Reverse | 5'-AGA ACC TGC CGT TGC GAG AA-3' SEQ ID NO: 8 | |
| 2 | Outer Forward | 5'-TCC ACA GTG ACC AGT CTC AT-3' SEQ ID NO: 9 | 333 bp |
| | Outer Reverse | 5'-GAT GGC AGT GAC GCG TGT CT-3' SEQ ID NO: 10 | |
| | Inner Forward | 5'-TGA GTG CAG AGG TGG CAG AA-3' SEQ ID NO: 11 | |
| | Inner Reverse | 5'-GTG ACG CGT GTC TGG AGG TT-3' SEQ ID NO: 12 | |
| 3 | Outer Forward | 5'-GCA GGC ACA GAT TCA ACA AG-3' SEQ ID NO: 13 | 381 bp |
| | Inner Reverse | 5'-GCA ACT GCT GAA TAG CCA AGT C-3' SEQ ID NO: 14 | |
| 4 | Outer Forward | 5'-GGC TGG GAT AGT GCA GCA ACA GCA G-3' SEQ ID NO: 15 | 485 bp |
| | Outer Reverse | 5'-AAG CGG GAG GGG AAG AGA ACA CTG GCC-3' SEQ ID NO: 16 | |
| | Inner Forward | 5'-TGT TGG ACG TGG TCA AGA GAC AAC-3' SEQ ID NO: 17 | |
| | Inner Reverse | 5'-GGG AGG GGA AGA GAA CAC TGG CCT ATA-3' SEQ ID NO: 18 | |
| 5 | Outer Forward | 5'-GAG AAG AAG ACG GTG GAG AA-3' SEQ ID NO: 19 | 341 bp |
| | Inner Reverse | 5'-GGA TTG CGA GTA TCC ATC TTC C-3' SEQ ID NO: 20 | |

TABLE 3

HIV-2NWK08F LTR-Gag Primers

| | Primer | Primer Sequence | PCR Fragment Size |
|---|---|---|---|
| 1 | Outer Forward | 5'-AGA AGG CTA GCC GCA AGA GG-3' SEQ ID NO: 21 | 511 bp |
| | Outer Reverse | 5'-TAC CTT CAC GTC CCG CTC AG-3' SEQ ID NO: 22 | |
| | Inner Forward | 5'-GAC ACA GCA GGG ACT TTC CA-3' SEQ ID NO: 23 | |
| | Inner Reverse | 5'-TTC CTC CGT CGC GGT TGG TT-3' SEQ ID NO: 24 | |
| 2 | Outer Forward | 5'-ACT CCT GAG TAC GGC TGA GT-3' SEQ ID NO: 25 | 318 bp |
| | Outer Reverse | 5'-CAA CAG GTC TTC TGC CAA TC-3' SEQ ID NO: 26 | |
| | Inner Forward | 5'-GGC TGA GTG AAG GCA GTA AG-3' SEQ ID NO: 27 | |
| | Inner Reverse | 5'-TCT GCC AAT CCG AAT CTG TC-3' SEQ ID NO: 28 | |

TABLE 3 -continued

HIV-2NWK08F LTR-Gag Primers

| Primer | | Primer Sequence | PCR Fragment Size |
|---|---|---|---|
| 3 | Outer Forward | 5'-TGG GAG ATG GGC GCG AGA AAC TCC GTC-3' SEQ ID NO: 29 | 809 bp |
|   | Outer Reverse | 5'-TCC ACA TTT CCA GCA GCC CTG TCT TCT-3' SEQ ID NO: 30 | |
|   | Inner Forward | 5'-AGG GAA GAA AGC AGA TGA ATT AGA A-3' SEQ ID NO: 31 | |
|   | Inner Reverse | 5'-GCA TTT TGA ATC AGC AGT GTT TGA GTC ATC CA-3' SEQ ID NO: 32 | |
| 4 | Outer Forward | 5'-ACG CAC AGC ATC CAA G-3' SEQ ID NO: 33 | 545 bp |
|   | Outer Reverse | 5'-CTT GAG CCA TGG GGA AAT TG-3' SEQ ID NO: 34 | |
|   | Inner Forward | 5'-GGA GAT GGA TTC AGC TAG GA-3' SEQ ID NO: 35 | |
|   | Inner Reverse | 5'-GGG GCT TCT TTC CCC ATG GAC C-3' SEQ ID NO: 36 | |

In exemplary embodiments, the nucleic acid comprises at least six nucleic acids derived from the HIV-2NWK08F genome. In particular embodiments, the nucleic acid comprises at least 6, 8, 10, 12, 15, 20, 25, 30, 40, or 50 consecutive nucleotides derived from the HIV-2NWK08F genome. In some embodiments, the nucleic acid comprises at least 6, 8, 10, 12, 15, 20, 25, 30, 40, or 50 consecutive nucleotides of SEQ ID NO:1 or SEQ ID NO:4. In some embodiments, the nucleic acid is no longer than about 50, 75, 100, or 200 nucleotides. In another embodiment, the nucleic acids of the invention encode a viral protein or fragment thereof, wherein the viral protein or fragment possesses the biological activity associated with the protein.

In some embodiments, the nucleic acids of the invention are attached to a detectable label. Examples of detectable labels include, but are not limited to, chromogens, radioisotopes, chemiluminescent compounds, visible or fluorescent particles, and enzymes. In the case of enzymes labels (e.g., alkaline phosphatase or horseradish peroxidase), addition of a chromo-, fluoro-, or lumogenic substrate results in the generation of a detectable signal.

The nucleic acids of the invention may be used to differentially detect HIV-2NWK08F from other subtype F HIV-2 viruses or from other HIV-1, HIV-2, or SIV strains. Alternatively, the nucleic acids of the invention may be used to detect any HIV or SIV strain. One of skill in the art would understand how to design primers and probes so as to preferentially detect HW-2NWK08F or to detect all HIV and SIV strains. Briefly, one could examine the sequences of a number of HIV and SIV strains and select regions of high or low homology. If the primers and probes are to preferentially detect HIV-2NWK08F, they are derived from regions of the genome with low homology to other strains and subtypes. Examples of regions with low homology include regions encoding the Env polypeptide. If the primers and probes are to detect all or some other HIV or SIV strains, they are derived from regions of the genome with high homology to other strains and subtypes. Examples of regions with high homology between strains include regions encoding the viral reverse transcriptase.

As used herein, a nucleic acid with a designated sequence or "derived from" a designated source refers to a nucleotide sequence that is homologous (i.e., identical) to or complementary to the designated sequence or source, or a portion thereof.

The nucleic acids of the invention may be produced by any method known to one of skill in the art. In exemplary embodiments, the nucleic acids are isolated from cells infected with HIV-2NWK08F.

Methods for isolating viral RNA or DNA are well known in the art. An exemplary method for extracting viral RNA or DNA from infected cells is described in Laure et al., *Lancet* 2(8610):538-41 (1988), the contents of which are incorporated by reference herein. Because infected cells contain copies of reverse transcribed viral DNA while whole virions contain only viral DNA, the methods for extracting the two nucleic acids differ slightly. To extract viral DNA, infected cells are separated from other blood constituents by centrifugation in a gradient, such as, e.g., a Ficoll gradient. The cells are lysed in a appropriate lysis buffer (e.g., 10 mM Tris pH 8, 10 mM EDTA, 10 mM NaCl, 0.5% SDS, 100 μg/mg proteinase K) for approximately 2 hours at 60° C. The DNA is then extracted with phenol and precipitated with ethanol. To isolate viral RNA, the same procedure is carried out on the serum, plasma, or blood leukocytes of infected patients or on the supernatant of infected cell cultures. Once extracted, the RNA may be transformed from single stranded RNA to double stranded DNA by performing a reverse transcriptase reaction, such as that described in U.S. Pat. No. 6,020,123, incorporated by reference herein.

The nucleic acids of the invention may also be produced recombinantly. Briefly, the nucleic acid is inserted into a vector and amplified in a host organism. Suitable vectors can be chosen or constructed, containing appropriate regulatory sequences. Vectors may be plasmids or viral, e.g., phage or phagemid, as appropriate. Many known techniques and protocols for manipulation of nucleic acid in preparation of nucleic acid constructs, mutagenesis, sequencing, introduction of DNA and/or vectors into cells, gene expression, and analysis of proteins are described in detail in Sambrook & Russell, *Molecular Cloning: A Laboratory Manual*, CSHL Press, 2001, the contents of which are incorporated by reference herein.

Alternatively, the nucleic acid may be amplified via the polymerase chain reaction using any of the exemplary primers disclosed herein or other primers derived from the nucleotide sequence of HIV-2NWK08F or another HIV virus (e.g., a different HIV-2 subtype F virus, a different HIV-2 subtype virus, or an HIV-1 or SIV virus). Methods for practicing nucleic acid amplification are described in Sambrook & Russell, *Molecular Cloning: A Laboratory Manual*, CSHL Press, 2001. Finally, the nucleic acids of the invention may be chemically synthesized using well know methods available from numerous commercial vendors, including, by not limited to, Applied Biosystems and Integrated DNA Technologies. Methods for purifying and handling chemically synthesized nucleic acids are described in Sambrook & Russell, *Molecular Cloning: A Laboratory Manual*, CSHL Press, 2001.

Polypeptides

The invention also provides amino acid sequences of HIV-2NWK08F polypeptides. The polypeptides of the invention are useful for detecting the presence of HIV-2NWK08F-specific antibodies in patient serum. The polypeptides of the invention are also useful for generating HIV-2NWK08F-specific antibodies. The polypeptides may be naturally occurring, recombinantly produced, or synthetic.

In exemplary embodiments, the polypeptides of the invention comprise at least six consecutive amino acids derived from a polypeptide encoded by the HIV-2NWK08F genome. In particular embodiments, the polypeptide comprises at least 6, 8, 6, 8, 10, 12, 15, 20, 25, 30, 40, or 50 consecutive amino acids derived from HIV-2NWK08F. In some embodiments, the polypeptide comprises at least 6, 8, 6, 8, 10, 12, 15, 20, 25, 30, 40, or 50 consecutive amino acids of SEQ ID NO:2, SEQ ID NO:3, SEQ ID NO:5, or SEQ ID NO:6. In some embodiments, the polypeptide is no longer than about 10, 11, 12, 13, 14, 15, 25, 50, 75, 100, 200, 300, 400, or 1000 amino acids. In other embodiments, the polypeptides comprises an entire viral protein, or a fragment thereof, wherein the viral protein or fragment possesses the biological activity associated with that protein.

An amino acid sequence derived from a designated polypeptide or source means that the amino acid sequence is homologous (i.e., identical) to the sequence of the designated polypeptide, or a portion thereof. An amino acid sequence from a designated nucleic acid sequence refers to a polypeptide having an amino acid sequence identical to that of a polypeptide encoded in the sequence, or a portion thereof.

The term "polypeptide" refers to a polymer of amino acids and does not refer to a specific length; thus, peptides, oligopeptides, and proteins are included within the definition of polypeptide. This term does not exclude post-expression modifications of the polypeptide, for example, glycosylation, acetylation, phosphorylation, pegylation, addition of a lipid moiety, or the addition of any organic or inorganic molecule. Included within the definition are, for example, polypeptides containing one or more analogs of an amino acid (including, for example, unnatural amino acids) and polypeptides with substituted linkages, as well as other modifications known in the art, both naturally occurring and non-naturally occurring.

In some embodiments, the polypeptides of the invention are derived from HIV-2NWK08F Gag or Env polypeptides or fragments thereof. In some embodiments, the polypeptides of the invention are immunogenic. In particular embodiments, the polypeptides of the invention comprise SEQ ID NO:2, SEQ ID NO:3, SEQ ID NO:5, or SEQ ID NO:6, or fragments thereof.

The polypeptides of the invention may be prepared by any method known to one of skill in the art, including those described in Sambrook & Russell, *Molecular Cloning: A Laboratory Manual*, CSHL Press, 2001, the contents of which are incorporated by reference herein. The polypeptides may be recombinantly expressed and purified. For example, DNA encoding the desired polypeptide may be ligated into an expression vector for any convenient host, either eukaryotic or prokaryotic. The polypeptide is expressed in a culture of the host cells and then isolated from lysed cells or the culture medium and purified.

Alternatively, the polypeptides of the invention may be isolated from infected cell cultures and purified. The purification of the polypeptides may be performed by techniques known in the art, such as, e.g., differential extraction, salt fractionation, cetrifugation, and ion exchange, affinity, or size exclusion chromatography.

Polypeptides of the invention may also be produced by chemical synthesis. For example, the polypeptides may be prepared with solid-phase synthesis such as that described in Bodansky et al., *The Practice of Peptide Synthesis*, Springer-Verlag, 1994.

Antibodies

The invention also provides HIV-2NWK08F-specific antibodies. The antibodies may be generated against the entire virion or against a specific polypeptide, including both whole proteins and peptide fragments. The antibodies of the invention are useful for the detection of HIV-2NWK08F infection in patients or cell culture, for the detection of HIV-2NWK08F antigens or virions, and for the treatment of patients infected with HIV-2NWK08F or similar viruses. The antibodies of the invention may also be used as therapeutics for the treatment of HIV infection. In a non-limiting example, antibodies specific for the HIV-2NWK08F Env protein may be used to prevent the binding of the Env protein to cells.

The term "antibody" as used herein includes polyclonal antibodies, monoclonal antibodies, antibody compositions with polyepitope specificities, bispecific antibodies, diabodies, humanized antibodies, and other purified preparations of antibodies and recombinant antibodies. The antibodies can be whole antibodies of any isotype, e.g., IgG, IgA, IgE, IgM, etc, or fragments thereof, which bind the antigen of interest. In a specific example of an antibody used in the present invention, the antibody is an IgG antibody. Antibodies can be fragmented using conventional or other techniques and the fragments screened for binding to an antigen of interest. Generally, an antibody fragment comprises the antigen-binding and/or the variable region of an intact antibody.

The term "antibody fragment" includes segments of proteolytically cleaved or recombinantly prepared portions of an antibody molecule that can selectively bind to a selected protein. Non-limiting examples of such proteolytic and/or recombinant fragments include Fab, $F(ab\gamma)_2$, Fabγ, Fv, and single chain antibodies (scFv) containing a V[L] and/or V[H] domain joined by a peptide linker, domain antibodies (dAbs), Nanobodies® (antibody-derived biological therapeutic agents that contain the unique structural and functional properties of naturally-occurring heavy-chain antibodies), and UniBodies (antibodies lacking the hinge region). The scFvs may be covalently or noncovalently linked to form antibodies having two or more binding sites.

The term "antigen" refers to any part of a virus that an antibody may specifically bind to. This includes polypeptides and modifying groups, such as glycoproteins, that may be attached to the polypeptides. It may include the whole virus, part of a virus, a whole protein, or part of a protein. An antibody may only bind to a part of the antigen.

The term "epitope" refers to a portion of an antigen that is responsible for specific interactions with the antibody. An epitope may be a peptide of at least about 6, 8, 10, 11, 12, 13, or 15 amino acids in length.

Antibodies specific for polypeptides of the invention can be prepared by any technique known to one of skill in the art. For example, the antibodies of the invention can be prepared via traditional hybridoma techniques (Kohler and Milstein, *Nature* 256:495-499 (1975), incorporated by reference herein), recombinant DNA methods (U.S. Pat. No. 4,816,567, incorporated by reference herein), or phage display techniques using antibody libraries (Clackson et al., *Nature* 352: 624-628 (1991); Marks et al., *J Mol Biol* 222:581-597 (1991), both of which are incorporated by reference herein). For various other antibody production techniques, see Harlow et al., *Antibodies: A Laboratory Manual*, CSHL Press, 1988, the contents of which are incorporated by reference herein.

Viral Detection Assays

The nucleic acids, polypeptides, and antibodies of the invention are useful for the detection of the presence of HIV-2 in a biological sample. These assays may be used to detect the presence of HIV infection in a patient or to determine whether cultured cells have been infected with the virus. The presence of HIV-2NWK08F nucleic acids, polypeptides, or antibodies in a patient or in a cell culture is indicative of HIV infection. Due to the homology between different subtypes and strains of HIV, detection of HIV-2NWK08F nucleic acids, polypeptides, and antibodies may also be used to detect other HIV subtypes and strains. Alternatively, detection of HIV-2NWK08F nucleic acids, polypeptides, or antibodies in a patient or cell culture may be used to determine that the patient or cells are infected with HIV-2NWK08F, and not a different strain or subtype of HIV.

All of the viral detection assays of the invention involve a step of providing a biological sample suspected of being infected with HIV or of containing HIV nucleic acids, polypeptides or anti-HIV antibodies. Accordingly, the first step in the viral detection assays is the identification of an appropriate patient, mammal, or infected cell culture and providing a biological sample from that source.

"Biological sample" refers to a sample of tissue or fluid isolated from an individual, including but not limited to, for example, whole blood and components thereof, dried blood, plasma, serum, spinal fluid, lymph fluid, the external sections of the skin, respiratory, intestinal, and genitourinary tracts, tears, saliva, urine, milk, blood cells, tumors, organs, and also samples of in vitro cell culture constituents, including, but not limited to, putatively virally infected cells, cells putatively expressing viral polypeptides, cell components, conditioned medium resulting from the growth of cells in cell culture medium, and cell free supernatant of one of the tissues or fluids listed above.

Nucleic Acid-Based Assays

Nucleic acid probes and primers are useful in identification of the virus, further characterization of the viral genome, and detection of the virus in diseased individuals. Nucleic acid-based assays are a preferred method for measuring HIV viral load in infected patients. In nucleic acid-based assays, an essential step is the provision of both the detecting nucleic acid, such as a primer or a probe and the nucleic acid to be detected, such as viral RNA or DNA. Methods for preparing both the detecting nucleic acid and the nucleic acid to be detected are provided herein.

Methods for selecting probes and primers and determining the specificity of these nucleic acids are known to those of skill in the art. The sequence and length of the probe or primer will depend on the proposed use. If the probe or primer is to be used to differentially detect the presence of HIV-2NWK08F, the sequence of the probe or primer will be specific to this virus, i.e., derived from an area of the viral genome that is not conserved between virus subtypes or strains. Viral genes that show low levels of homology between subtypes and strains include the envelope gene. If the probe or primer is to be used to detect all HIV-2 viruses or all HIV viruses in general, it will be derived from an area of the viral genome that is conserved between virus subtypes or strains. Viral genes that show high levels of homology between subtypes and strains include certain regulatory proteins, such as, e.g., the genes encoding the viral reverse transcriptase.

For diagnostic use of probes, the biological sample to be analyzed, such as blood or serum, may be treated, if desired, to extract the nucleic acids contained therein. The resulting nucleic acid from the sample may be subjected to gel electrophoresis or other size separation techniques; alternatively, the nucleic acid sample may be dot blotted without size separation. The probes are then labeled. Suitable labels, and methods for labeling probes are known in the art, and include, for example, radioactive labels incorporated by nick translation or kinasing, biotin, fluorescent probes, and chemiluminescent probes. The nucleic acids extracted from the sample are then treated with the labeled probe under hybridization conditions of suitable stringencies. Usually high stringency conditions are desirable in order to prevent false positives. The stringency of hybridization is determined by a number of factors during hybridization and during the washing procedure, including temperature, ionic strength, length of time, and concentration of formamide. These factors are outlined in, for example, Sambrook & Russell, *Molecular Cloning: A Laboratory Manual*, CSHL Press, 2001.

If the HIV-2NWK08F genome sequences are present in serum of infected individuals at relatively low levels, detection may require that amplification techniques be used in hybridization assays. Such techniques are known in the art. A particularly desirable technique may first involve amplification of the target HIV-2NWK08F sequences in serum, plasma, or cells approximately 10,000-fold, i.e., to approximately $10^6$ sequences/ml. This may be accomplished, for example, by polymerase chain reactions (PCR). The amplified sequences may then be detected using a hybridization assay. These hybridization assays, which should detect sequences at the level of $10^6$ copies/ml, utilize nucleic acid multimers which bind to single-stranded analyte nucleic acid, and which also bind to a multiplicity of single-stranded labeled oligonucleotides. A suitable solution phase sandwich assay may be used with labeled polynucleotide probes.

The probes and primers of the invention may be used to quantitate viral nucleic acid levels by real-time PCR. Real-time PCR refers to a polymerase chain reaction that is monitored, usually by fluorescence, over time during the amplification process, to measure a parameter related to the extent of amplification of a particular sequence, such as the extent of hybridization of a probe to amplified target sequences. The initial nucleic acids of the reaction are synthesized from the RNA template using reverse transcriptase. Then the DNA generated within a PCR reaction is detected on a cycle by cycle basis during the PCR reaction. The amount of DNA increases with the amount of template sequences present in the original sample. When enough amplification products are made, a threshold is reached at which the PCR products are detected.

The HIV-2NWK08F probes and primers are a length that allows the detection of unique viral sequences by hybridization. These nucleic acids can be prepared using routine methods, including automated oligonucleotide synthetic methods. The nucleic acids may be a complement to any unique portion of the HIV-2NWK08F genome. For use as probes, complete complementarity is desirable, though it may be unnecessary as the length of the fragment is increased. Primers used in the methods of the invention include oligonucleotides of sufficient length and appropriate sequence to provide specific initiation of polymerization of a HIV or HIV-2NWK08F nucleic acid in a polymerase chain reaction (PCR). Conditions and reagents for performing nucleic acid amplification utilizing PCR and other nucleic acid amplification techniques are known to one of skill in the art and may be found in, e.g., Sambrook & Russell, *Molecular Cloning: A Laboratory*

*Manual*, CSHL Press, 2001. The nucleic acids that make up the probes or primers of the invention may be at least about, e.g., 6, 8, 10, 12, 15, 20, 25, 30, 40, or 50 nucleotides in length. The nucleic acids may have a maximum length of about, e.g., 50, 75, 100, or 200 nucleotides.

The probes and primers of the invention can be packaged into diagnostic kits. Diagnostic kits include the probe and/or primer nucleic acids, which may be labeled; alternatively, the probe or primer nucleic acids may be unlabeled and the ingredients for labeling may be included in the kit in separate containers. The kit may also contain other suitably packaged reagents and materials needed for the particular amplification and/or hybridization protocol, for example, standards, enzymes, nucleotide triphosphates, wash buffers, as well as instructions for conducting the test.

Immunoassays

Immunoassays may be used to detect anti-HIV-2NWK08F antibodies in patient serum or to detect HIV-2NWK08F-specific antigens in patient serum. Immunoassays can be used to test for the presence of HIV antibodies or antigens in blood, oral mucosal transudate (OMT) fluid, saliva, and urine, or cell-free supernatants of these fluids. Immunoassays are currently more commonly used for diagnosing HIV infection than nucleic acid assays.

HIV immunoassays include, but are not limited to, Western blot assays and enzyme-linked immunosorbent assays (ELISA). An immunoassay for viral antigen may use, for example, a monoclonal antibody directed towards a viral epitope, a combination of monoclonal antibodies directed towards epitopes of one viral polypeptide, monoclonal antibodies directed towards epitopes of different viral polypeptides, polyclonal antibodies directed towards the same viral antigen, polyclonal antibodies directed towards different viral antigens, or a combination of monoclonal and polyclonal antibodies.

An immunoassay for viral antibodies may use, for example, a HIV-2NWK08F viral antigen, such as, e.g., fragments of the Env, Pol, Gag, or Nef polypeptides.

Immunoassay protocols may be based, for example, upon competition, or direct reaction, or sandwich type assays. Protocols may also, for example, use solid supports, or may be by immunoprecipitation. Most assays involve the use of labeled antibody or polypeptide. The labels may be, for example, fluorescent, chemiluminescent, radioactive, or dye molecules. Assays which amplify the signals from the probe are also known. Examples of which are assays which utilize biotin and avidin, and enzyme-labeled and mediated immunoassays, such as ELISA assays.

Typically, an immunoassay for anti-HIV-2NWK08F antibody will involve selecting and preparing the test sample, such as a biological sample, and then incubating it with an antigenic (i.e., epitope-containing) HW-2NWK08F polypeptide under conditions that allow antigen-antibody complexes to form. Such conditions are well known in the art. The polypeptide may be bound to a solid support. Examples of solid supports that can be used are nitrocellulose in membrane or microtiter well form, polyvinylchloride in sheets or microtiter wells, polystyrene latex, in beads or microtiter plates, polyvinylidine fluoride (known as Immobilon™), diazotized paper, nylon membranes, activated beads, and Protein A beads. In certain embodiments, these assays are performed using either Immulon™ microtiter plates (Dynatech) or specular-finished 0.25-inch polystyrene beads (available from Precision Plastic Ball). The solid support is typically washed after separating it from the test sample.

In another embodiment, the test sample is incubated with antigen in solution under conditions that will precipitate any antigen-antibody complexes that are formed, as is known in the art. The precipitated complexes are then separated from the test sample by, for example, centrifugation. The complexes formed comprising anti-HIV-2NWK08F antibody are then detected by any of a number of techniques. Depending on the type of assay, the complexes can be detected with labeled anti-xenogeneic Ig or by measuring the amount of bound, labeled competing antibody.

In immunoassays where HIV-2NWK08F polypeptides are the analyte, the test sample, typically a biological sample, is incubated with anti-HIV-2NWK08F antibodies again under conditions that allow the formation of antigen-antibody complexes. Various formats can be employed, such as the "sandwich" assay. In this assay, antibody is bound to a solid support, incubated with a test sample, washed, incubated with a labeled anti-analyte antibody, and washed again. Analyte is detected by determining if the second antibody is bound to the support. In a competitive format, which can be either heterogeneous or homogeneous, a test sample is usually incubated with and antibody and a labeled, competing antigen either sequentially or simultaneously. These and other formats are well known in the art.

Treatment of Infected Patients

This invention also provides methods of treating patients infected with HIV-2NWK08F. Methods of treating HIV infections are known in the art. Patients infected with HIV-2NWK08F can be treated by any known anti-HIV therapeutic, such as those described in Panel on Antiretroviral Guidelines for Adults and Adolescents. Guidelines for the use of antiretroviral agents in HIV-1-infected adults and adolescents. Department of Health and Human Services. Jan. 29, 2008; 1-128, incorporated by reference herein. The invention also provides methods of treating opportunistic infections that accompany the immunosuppression caused by HIV infection. These opportunistic diseases and their treatments are described in Panel on Guidelines for the Prevention and Treatment of Opportunistic Infections in HIV-Infected Adults and Adolescents. Guidelines for Prevention and Treatment of Opportunistic Infections in Adults and Adolescents. Department of Health and Human Services. Jun. 20, 2008; 1-302, incorporated by reference herein.

In addition, the HIV-2NWK08F virus, nucleic acids, and proteins of the invention may be used to develop new therapeutic antibodies and vaccines for the treatment of HIV-2 infections. The vaccines may be derived from the whole virus, the virion, viral proteins, or viral nucleic acids.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLES

Example 1

Identification of Infected Patient

Patient X, a 68 year old man from Sierra Leone, tested positive for antibodies to HIV in a test that detects the presence of HIV-1 or HIV-2 antibodies. Subsequent testing for HIV-1 antibodies in a Western blot showed that the patient was not infected with HIV-1. His HIV-1 viral load was tested in an Real-time Polymerase Chain Reaction (RT-PCR) assay (LabCorp) and was below the lower limit of the assay. HIV-2 viral DNA testing performed at two commercial laboratories (Viromed; Focus Technologies) was negative, as was an HIV-2 Western blot. HIV-2 viral DNA was finally detected with the use of primers derived from HIV-2 subtype F (as described in Example 3).

Example 2

Isolation and Propagation of HIV

Normal donor PBMCs were stimulated with PHA at 5 µg/ml for three days and then re-suspended in RPMI supplemented with 10% fetal bovine serum and 20 units/ml of IL-2. To isolate the virus, these stimulated normal donor PBMCs were then co-cultured with PBMCs from Patient X. The culture was split every 3-4 days and supernatant was collected for p27 measurement by EIA for SW p27 (Zeptometrix), which detected the p27 protein of HIV-2NWK08F. PBMCs were collected at each time point and their DNA was extracted.

This co-culturing process was performed with three different populations of normal donor PBMCs. HW-2NWK08F virus replicated each time, with the peak p27 concentration exceeding 10 µg/ml in each co-culture (tested with Zeptometrix SW p27 kit).

Example 3

Amplification and Sequencing of Viral RNA

Portions of the gag and env genes were amplified as described in Chen et al., *J Virol* 71:3953-3960 (1997). Briefly, DNA was extracted from each PBMC culture on day 13 using a DNA extraction kit (Qiagen, Valencia, Calif.). Nested primers were used to amplify a 438-bp env fragment. Traditional polymerase chain reaction (PCR) was performed in a Tpersonal thermocycler (Biometra, Hannover, Germany) using a PCR Master Mix Kit (Applied Biosystems, Foster City, Calif.). These reactions were performed in a 50 µl volume which contained approximately 350 ng of DNA and 20 pmol of each primer. The first round of PCR had an initial activation step at 95° C. for 5 minutes followed by 30 cycles of 95° C. for 20 seconds, 45° C. for 1.5 minutes, and 72° C. for 2 minutes with env outer primer pair EF-1 and ER-1. The second round of PCR was performed using inner primers EF-2 and ER-2. This round consisted of 30 cycles of 94° C. for 20 seconds, 55° C. for 1.5 minutes, and 72° C. for 2 minutes. Additionally, both rounds of PCR consisted of an extension step at 72° C. for 8 minutes.

```
                                              (SEQ ID NO: 37)
EF-1:  GGCTGGGATAGTGCAGCAACAGCAACAG (SEQ ID NO: 38)
ER-1:  GGGAGGGGAAGAGAACACTGGCCTATA (SEQ ID NO: 39)
EF-2:  TGTTGGACGTGGTCAAGAGACAAC (SEQ ID NO: 40)
ER-2:  AAGCGGGAGGGGAAGAGAACACTGGCC
```

The same procedure was used to amplify a 826 bp gag fragment using the following primers:

```
                                              (SEQ ID NO: 41)
GF-1:  TGGGAGATGGGCGCGAGAAACTCCGTC (SEQ ID NO: 42)
GR-1:  TCCACATTTCCAGCAGCCCTGTCTTCT (SEQ ID NO: 43)
GF-2:  AGGGAAGAAAGCAGATGAATTAGAA (SEQ ID NO: 44)
GR-2:  GCATTTTGAATCAGCAGTGTTTGAGTCATCCA
```

The gag and env PCR products were cloned and sequenced as described in Chen et al., *J Virol* 70:3617-27 (1996).

Example 4

Phylogenetic Analysis

Gag and Env nucleotide sequence alignments were obtained from the Los Alamos National Laboratory HIV Sequence Database Newly derived HIV-2NWK08F sequences were aligned using the CLUSTAL W profile alignment option. The resulting alignments were adjusted manually when necessary. Regions of ambiguous alignment and all gap-containing sites were excluded.

Figure 1:
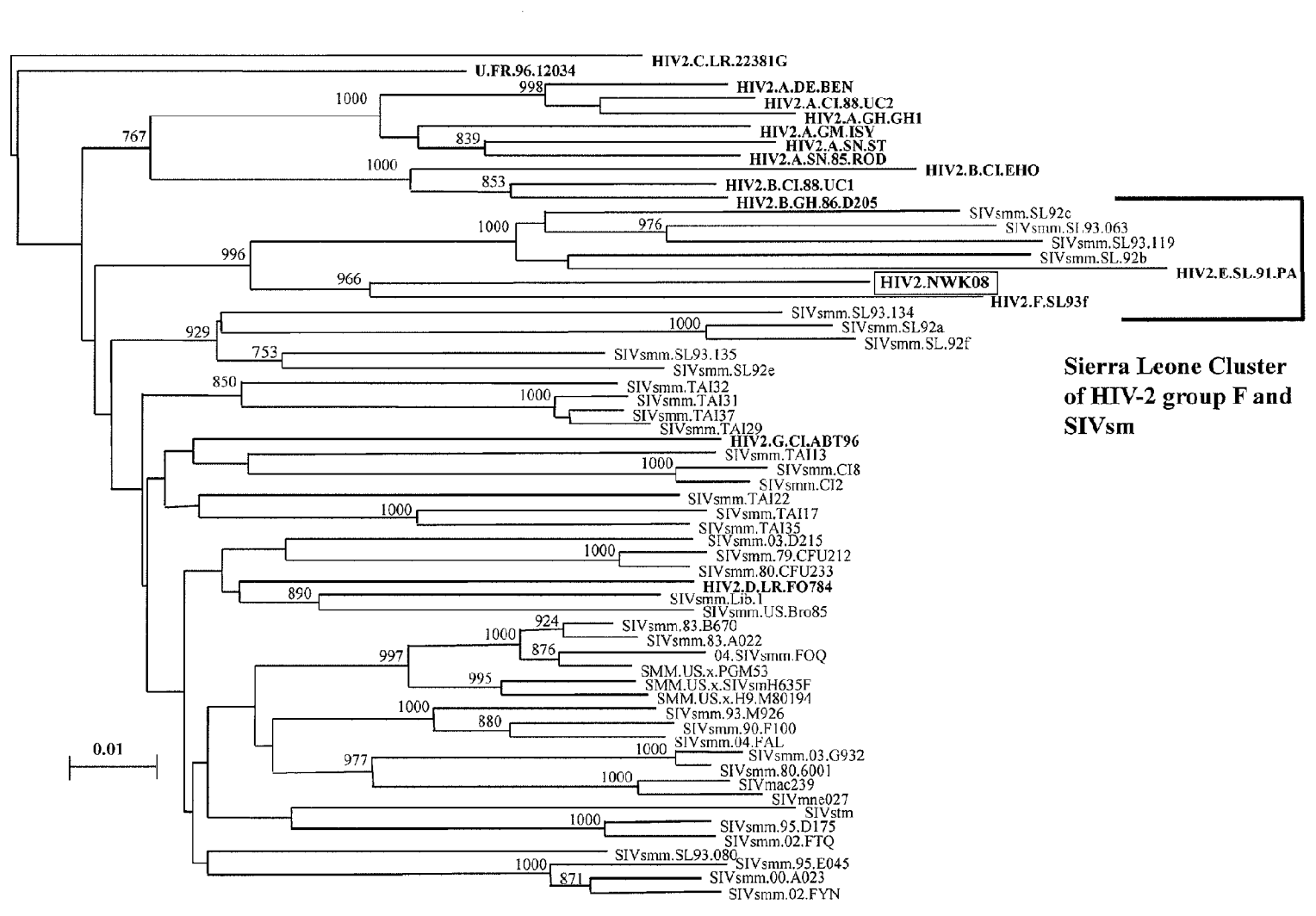

Phylogenetic trees were inferred from the nucleotide sequence alignments by the neighbor-joining method, using the HKY85 model of nucleotide substitution implemented in PAUP*. The reliability of the branching order was assessed by performing 1,000 bootstrap replicates, again using neighbor joining and the HKY85 model. Phylogenetic trees were also inferred by the maximum likelihood method, using PAUP* with models inferred from the alignment by the use of Modeltest (Posada, et al., *Syst Biol* 50:580601 (2001); Swofford, PAUP*. Phylogenetic analysis using parsimony (*and other methods), version 4. Sinauer Associates, Sunderland, Mass. (1999)). These trees are shown in FIGS. 1 and 2.

Example 5

Detection of Anti-HIV Antibodies in Patient Serum

A sample of Patient X's blood was sent to LabCorp® of Burlington, N.C. for detection of HIV antibodies. The assay used to assess the presence of HIV-1 antibodies was Protocol Number 005462, a Western blotting procedure that detects antibodies to Gp41, Gp120, Gp160, p18, p24, p31, p40, p51, p55, and p64. This Western blot for HIV-1 antibodies was negative. HIV-2 antibodies were positively detected using Protocol Number 163550, an Enzyme Immunoassay (EIA) that differentially detects antibodies to HIV-2, but not HIV-1.

Example 6

Real Time Reverse Transcription-PCR for HIV-2 Proviral Load

Proviral DNA from PBMCs was isolated using a DNA extraction kit from QIAGEN®. The DNA quality was confirmed with a spectrophotometer. 48 ng and 480 ng of DNA was subsequently quantified with real time PCR using the following primers and probe derived from the HIV-2NWK08F env gene.

```
                                              (SEQ ID NO: 45)
Forward Primer    AAGAATTGTTGCGATTGACAGTCT (SEQ ID NO: 46)
Reverse Primer    TGCACACCCCCATGAATTTA (SEQ ID NO: 47)
Probe             ACTAAAAACCTCCAGACACGCGTCACTGC
```

The PCR was performed in TaqMan Universal PCR Master Mix on an Applied Biosystems 7300 Real time PCR System (Applied Biosystems, Foster City, Calif.). The real time PCR conditions were as described in Table 4.

TABLE 4

| Stage | Temperature (° C.) | Time (min:secs) | Repeat |
|---|---|---|---|
| 1 | 50 | 2:00 | 1 |
| 2 | 95 | 10:00 | 1 |
| 3 | 95 | 0:15 | 40 |
|   | 60 | 1:00 |   |

The real time PCR data were analyzed using the 2-ΔΔCT method according to the manufacturer's directions. Patient X had a proviral load of 6,100 copies per $10^6$ PBMC.

Example 7

Measuring Patient T-Cell Counts

Patient X's blood was sent to LabCorp® for measurement of CD4 and CD8 T cell levels. The CD4 T cell levels and CD4:CD8 ratios were determined by Protocols 505008 and 505271, respectively. Patient X had a CD4 T-cell count of 338 cells/μl and a CD4:CD8 ratio of 0.52.

What is claimed is:

1. An isolated human immunodeficiency virus type 2 (HIV-2) comprising the virus deposited as HIV-2NWK08F, said virus having ATCC accession number PTA-9773.

2. An isolated HIV-2NWK08F virus comprising the nucleotide sequence of SEQ ID NO:1 or SEQ ID NO:4.

* * * * *

SEQUENCE LISTING

<160> NUMBER OF SEQ ID NOS: 47

<210> SEQ ID NO 1
<211> LENGTH: 1417
<212> TYPE: DNA
<213> ORGANISM: Human immunodeficiency virus

<400> SEQUENCE: 1

```
taccttcatg tggacaaatt gcagaggaga atttttatat tgtaaaatga attggttcct    60
aaattgggta gaagacagaa atataactca tggaagatgg agtactcaaa aaccagcaga   120
gaaacagaag aggaactatg tgccttgcca cataaggcaa atcataaata cttggcacaa   180
agtagggaaa aatgtgtacc tgcctccaag agaaggtaat ctaacgtgta actcatcagt   240
aacaagcata attgcaaaca tagactggac aagcgacaat gaaactaata tcaccatgag   300
tgcagaagtg gcagaactgt atcgattaga gttgggtgac tataaattag tagagataac   360
accaattggc ttggccccaa cagaagtaaa aagatattcc tcagcaacac cgaggaataa   420 gagagggtc tttgtgctag ggttcttggg atttctcgca acggcaggtt ctgcaatggg   480
cgcagcgtcg ctgacgctga cagctcagtc tcggacttta ctggctggga tagtgcagca   540
acagcagcag ctgttggatg cagtcaagag acaacaagaa ttgttgcgat tgacagtctg   600
ggggactaaa aacctccaga cacgcgtcac tgccatcgag aaatacctaa aggatcaggc   660
acagctaaat tcatggggt gtgcatttag acaggtctgc catactactg taccatggcc   720
aaatgacaca ttgcaaccaa attgggacaa catgacttgg caagagtggg aaaggaaagt   780
agactttctc acagaaaaca tcacagaact cttggagcag gcacagattc aacaagaaaa   840
aaatatgtat gaactacaaa aattgaacag ctgggatgtg tttggcaatt ggtttgacct   900
cagctcctgg atcacctaca tacagtatgg agtatactta gtagtaggag taatagggct   960
tagaataagt atatatatag tacagatgct attgaggctt agaaagggct ataggcccgt  1020
gttctcttcc ccaccctctt atcgccagca gatccatatc cgacgggacc aggaactgcc  1080
agacggagaa gacagagaag aagacggtgg agaaaaaggt ggcaacagat cctggccctg  1140
gcagatagag tacattcatt tcctgatccg ccagttgatt cgcctcttga cttggctata  1200
cagcaattgc agagacttaa tatacaagag cttccagacc ctccaccagc tgaccagtgc  1260
agcagcaaca gcaactagag actttatcag aacagaagcc agttacatca gctatgggtg  1320
gcaatacttc ctcgaagccc tccaagcggc aatgcagact gcgggagaga ctcttgcaag  1380
cgcgggggga gaattatggg caactctggg aaggatt                           1417
```

```
<210> SEQ ID NO 2
<211> LENGTH: 470
<212> TYPE: PRT
<213> ORGANISM: Human immunodeficiency virus

<400> SEQUENCE: 2

Met Trp Thr Asn Cys Arg Gly Glu Phe Leu Tyr Cys Lys Met Asn Trp
1               5                   10                  15

Phe Leu Asn Trp Val Glu Asp Arg Asn Ile Thr His Gly Arg Trp Ser
            20                  25                  30

Thr Gln Lys Pro Ala Glu Lys Gln Lys Arg Asn Tyr Val Pro Cys His
        35                  40                  45

Ile Arg Gln Ile Ile Asn Thr Trp His Lys Val Gly Lys Asn Val Tyr
    50                  55                  60

Leu Pro Pro Arg Glu Gly Asn Leu Thr Cys Asn Ser Ser Val Thr Ser
65                  70                  75                  80

Ile Ile Ala Asn Ile Asp Trp Thr Ser Asp Asn Glu Thr Asn Ile Thr
                85                  90                  95

Met Ser Ala Glu Val Ala Glu Leu Tyr Arg Leu Glu Leu Gly Asp Tyr
            100                 105                 110

Lys Leu Val Glu Ile Thr Pro Ile Gly Leu Ala Pro Thr Glu Val Lys
        115                 120                 125

Arg Tyr Ser Ser Ala Thr Pro Arg Asn Lys Arg Gly Val Phe Val Leu
    130                 135                 140

Gly Phe Leu Gly Phe Leu Ala Thr Ala Gly Ser Ala Met Gly Ala Ala
145                 150                 155                 160

Ser Leu Thr Leu Thr Ala Gln Ser Arg Thr Leu Leu Ala Gly Ile Val
                165                 170                 175

Gln Gln Gln Gln Gln Leu Leu Asp Ala Val Lys Arg Gln Gln Glu Leu
            180                 185                 190

Leu Arg Leu Thr Val Trp Gly Thr Lys Asn Leu Gln Thr Arg Val Thr
        195                 200                 205

Ala Ile Glu Lys Tyr Leu Lys Asp Gln Ala Gln Leu Asn Ser Trp Gly
    210                 215                 220

Cys Ala Phe Arg Gln Val Cys His Thr Thr Val Pro Trp Pro Asn Asp
225                 230                 235                 240

Thr Leu Gln Pro Asn Trp Asp Asn Met Thr Trp Gln Glu Trp Glu Arg
                245                 250                 255

Lys Val Asp Phe Leu Thr Glu Asn Ile Thr Glu Leu Leu Glu Gln Ala
            260                 265                 270

Gln Ile Gln Gln Glu Lys Asn Met Tyr Glu Leu Gln Lys Leu Asn Ser
        275                 280                 285

Trp Asp Val Phe Gly Asn Trp Phe Asp Leu Ser Ser Trp Ile Thr Tyr
    290                 295                 300

Ile Gln Tyr Gly Val Tyr Leu Val Val Gly Val Ile Gly Leu Arg Ile
305                 310                 315                 320

Ser Ile Tyr Ile Val Gln Met Leu Leu Arg Leu Arg Lys Gly Tyr Arg
                325                 330                 335

Pro Val Phe Ser Ser Pro Pro Ser Tyr Arg Gln Gln Ile His Ile Arg
            340                 345                 350

Arg Asp Gln Glu Leu Pro Asp Gly Glu Asp Arg Glu Glu Asp Gly Gly
        355                 360                 365

Glu Lys Gly Gly Asn Arg Ser Trp Pro Trp Gln Ile Glu Tyr Ile His
    370                 375                 380
```

```
Phe Leu Ile Arg Gln Leu Ile Arg Leu Leu Thr Trp Leu Tyr Ser Asn
385                 390                 395                 400

Cys Arg Asp Leu Ile Tyr Lys Ser Phe Gln Thr Leu His Gln Leu Thr
            405                 410                 415

Ser Ala Ala Ala Thr Ala Thr Arg Asp Phe Ile Arg Thr Glu Ala Ser
            420                 425                 430

Tyr Ile Ser Tyr Gly Trp Gln Tyr Phe Leu Glu Ala Leu Gln Ala Ala
            435                 440                 445

Met Gln Thr Ala Gly Glu Thr Leu Ala Ser Ala Gly Gly Glu Leu Trp
            450                 455                 460

Ala Thr Leu Gly Arg Ile
465                 470

<210> SEQ ID NO 3
<211> LENGTH: 34
<212> TYPE: PRT
<213> ORGANISM: Human immunodeficiency virus

<400> SEQUENCE: 3

Met Gly Gly Asn Thr Ser Ser Lys Pro Ser Lys Gln Cys Arg Leu
1               5                   10                  15

Arg Glu Arg Leu Leu Gln Ala Arg Gly Glu Asn Tyr Gly Gln Leu Trp
                20                  25                  30

Glu Gly

<210> SEQ ID NO 4
<211> LENGTH: 2663
<212> TYPE: DNA
<213> ORGANISM: Human immunodeficiency virus

<400> SEQUENCE: 4
tggaagggat gttttacagt gagaggaggc atagaatatt agacacatac ttagaaaagg      60
aggaaggaat agttccagat tggcagaatt atacacgggg accaggtatt agatatccaa     120
aatactttgg ctggctatgg cagctggaac cagtggacgt ctcagaagaa atgatgaga     180
caaattgtct ggtccatcca gcgcagacaa gtcagtggga cgacccatgg ggggaaactc     240
tagtatggag atttaattct gcattggctt acacctatga gcttacatt agacatccag     300
aagagtttgg ttggaagtga ggcctgtcag aggaagaggt taagcagaga ctggctgaca     360
ggaagaagcc aaccacaaag taagatggcg gacagaaagg aaactagctg atatagcagg     420
gactttccaa caaggggacg ggcaatgggt ggagactggg cgggggtat gggaacgccc     480
cattttactc tgtataaatg tacccgctta ctgctctgta atcagtcgct ctgcggagag     540
gctgccaggt agagccccga gtggatccct ggtagcacta gcaggagagc ctgggtgttc     600
cctgctagac tctcactggt gcttggccag taccaggcag acggctccac gcttgcttgc     660
ttgactctca ataaagctgc catttagaag caagtcagcg tgtgttccca tctcttctag     720
tcgccgcctg gtcattcggt gtcctggctc gaggtctcgg tatcaagtcc ctggaactgt     780
cagaaccctc tcactaaggg gcaacccgta gtgaaaaatc tctggcagtt tggcgcccga     840
acagggacat gagagacctg agaaagcaca cggctgagtg aaggcagcaa gggcggcaga     900
aaccaaccgc gacggaggaa gacccggtgc cagggggctg agcgggacgt gaaggtaaga     960
gaggccttcg ggacagatag tccaaagttt gtgtagctat agagctgttt ccctacccctc    1020
aaggagggta gaagtatagc gggagatggg cgcgagacac tccgtcttgt cagggaaaaa    1080
agcagatgaa ttagaaaaag ttaggttacg gcccggcgga agaaaaagt atatgttaaa     1140
```

```
gcatataata tgggcagcaa aagaattgga cagattcgga ttggcagaag acctgttgga    1200
aaacaaacaa ggatgtcaaa gaatattaga agttttaacc ccattaatgc caacaggctc    1260
agaaaattta aagagtttgt ataatactgt ctgcgtagtt tggtgtttgc acgcagaaga    1320
gaaagtgaaa cacacagagg aagcaaagca gttggtacag agacatctag tggcagaaac    1380
taaaactgca gaaaaatac cagcaaaaag tagaccaaca gctccaccta gtggaggaaa    1440
ttatccagtg cagcaagtag gtggaaatta tgtccactta ccattaagcc ccagaacttt    1500
aaatgcctgg gtaaaattag tagaggaaaa gaaatttgga gcagaagtag tgccaggctt    1560
tcaggcactg tcagaaggct gcacaccta tgatattaat cagatgctaa attgtgtagg    1620
ggaacatcaa gcggctatgc aaataattag agaaattatc aatgaggaag cagcagactg    1680
ggacgcacag catccaaggc agctaccggc acctccgggg ctgcgcgacc cgtcagggtc    1740
agatatagca ggaaccacca gtactgtaga agagcaaata gagtggatgt atagacaagg    1800
aaatcctgtc ccagtaggac aaatttacag agatgggatt cagctaggat acaaaaatg    1860 tgtaagaatg tacaatccca ctaacattct agacgtaaag caaggtccaa agagccatt    1920 ccaagtttat gtagacaggt tctacaaaag tttgagagca gaacaaacag acccagcagt    1980
gaagaattgg atgacccaaa cactgctgat ccaaaatgcc aaccctgatt gcaaactagt    2040
attaaaagga ttgggaatga atcccacctt agaagaaatg ttaacagctt gtcagggagt    2100
gggaggtcct ggacaaaagg ctaggttaat ggccgaggca atgaaggaag cctttaatgg    2160
ctccttcgcg gccgtgcaga tgagaggaa acaacagaag ggggcatcaa ctattagatg    2220
ctttaattgt gggaaaccag gccacactgc cagaaattgc agggcaccaa gaagaaggg    2280 gtgctggaaa tgtggagagg aaggacacat gcaagcaaac tgcccaaacc aacgggcggg    2340
ttttttaggg ttaggaccat ggggaagaa gcctcgcaac ttccccatga cagatgcc    2400 agagggactg accccatcag cccctccgga cccagcagca gaaatgctcg aggagtatat    2460
gcagaagggg aaaagtcaga gggagcagag ggagagacct acaaagagg tgacggagga    2520 cttgctgcac ctcagttctc tctttggaaa agaccagtag tcacagcata tagaggat    2580 cagccagtac aggtactgct agatacagga gctgatgact ctatagtggc agggatagaa    2640
ttaggactta attacaagcc aaa                                           2663
```

<210> SEQ ID NO 5
<211> LENGTH: 504
<212> TYPE: PRT
<213> ORGANISM: Human immunodeficiency virus

<400> SEQUENCE: 5

```
Met Gly Ala Arg His Ser Val Leu Ser Gly Lys Lys Ala Asp Glu Leu
1               5                   10                  15

Glu Lys Val Arg Leu Arg Pro Gly Gly Lys Lys Lys Tyr Met Leu Lys
            20                  25                  30

His Ile Ile Trp Ala Ala Lys Glu Leu Asp Arg Phe Gly Leu Ala Glu
        35                  40                  45

Asp Leu Leu Glu Asn Lys Gln Gly Cys Gln Arg Ile Leu Glu Val Leu
    50                  55                  60

Thr Pro Leu Met Pro Thr Gly Ser Glu Asn Leu Lys Ser Leu Tyr Asn
65                  70                  75                  80

Thr Val Cys Val Val Trp Cys Leu His Ala Glu Glu Lys Val Lys His
                85                  90                  95

Thr Glu Glu Ala Lys Gln Leu Val Gln Arg His Leu Val Ala Glu Thr
```

```
                    100                 105                 110
Lys Thr Ala Glu Lys Ile Pro Ala Lys Ser Arg Pro Thr Ala Pro Pro
                115                 120                 125
Ser Gly Gly Asn Tyr Pro Val Gln Gln Val Gly Gly Asn Tyr Val His
    130                 135                 140
Leu Pro Leu Ser Pro Arg Thr Leu Asn Ala Trp Val Lys Leu Val Glu
145                 150                 155                 160
Glu Lys Lys Phe Gly Ala Glu Val Val Pro Gly Phe Gln Ala Leu Ser
                165                 170                 175
Glu Gly Cys Thr Pro Tyr Asp Ile Asn Gln Met Leu Asn Cys Val Gly
            180                 185                 190
Glu His Gln Ala Ala Met Gln Ile Ile Arg Glu Ile Ile Asn Glu Glu
        195                 200                 205
Ala Ala Asp Trp Asp Ala Gln His Pro Arg Gln Leu Pro Ala Pro Pro
210                 215                 220
Gly Leu Arg Asp Pro Ser Gly Ser Asp Ile Ala Gly Thr Thr Ser Thr
225                 230                 235                 240
Val Glu Glu Gln Ile Glu Trp Met Tyr Arg Gln Gly Asn Pro Val Pro
                245                 250                 255
Val Gly Gln Ile Tyr Arg Arg Trp Ile Gln Leu Gly Leu Gln Lys Cys
                260                 265                 270
Val Arg Met Tyr Asn Pro Thr Asn Ile Leu Asp Val Lys Gln Gly Pro
            275                 280                 285
Lys Glu Pro Phe Gln Val Tyr Val Asp Arg Phe Tyr Lys Ser Leu Arg
        290                 295                 300
Ala Glu Gln Thr Asp Pro Ala Val Lys Asn Trp Met Thr Gln Thr Leu
305                 310                 315                 320
Leu Ile Gln Asn Ala Asn Pro Asp Cys Lys Leu Val Leu Lys Gly Leu
                325                 330                 335
Gly Met Asn Pro Thr Leu Glu Glu Met Leu Thr Ala Cys Gln Gly Val
                340                 345                 350
Gly Gly Pro Gly Gln Lys Ala Arg Leu Met Ala Glu Ala Met Lys Glu
            355                 360                 365
Ala Phe Asn Gly Ser Phe Ala Ala Val Gln Met Arg Gly Lys Gln Gln
        370                 375                 380
Lys Gly Ala Ser Thr Ile Arg Cys Phe Asn Cys Gly Lys Pro Gly His
385                 390                 395                 400
Thr Ala Arg Asn Cys Arg Ala Pro Arg Arg Lys Gly Cys Trp Lys Cys
                405                 410                 415
Gly Glu Glu Gly His Met Gln Ala Asn Cys Pro Asn Gln Arg Ala Gly
                420                 425                 430
Phe Leu Gly Leu Gly Pro Trp Gly Lys Lys Pro Arg Asn Phe Pro Met
            435                 440                 445
Arg Gln Met Pro Glu Gly Leu Thr Pro Ser Ala Pro Pro Asp Pro Ala
        450                 455                 460
Ala Glu Met Leu Glu Glu Tyr Met Gln Lys Gly Lys Ser Gln Arg Glu
465                 470                 475                 480
Gln Arg Glu Arg Pro Tyr Lys Glu Val Thr Glu Asp Leu Leu His Leu
                485                 490                 495
Ser Ser Leu Phe Gly Lys Asp Gln
                500

<210> SEQ ID NO 6
<211> LENGTH: 145
```

-continued

```
<212> TYPE: PRT
<213> ORGANISM: Human immunodeficiency virus

<400> SEQUENCE: 6

Met Trp Glu Thr Arg Pro His Cys Gln Lys Leu Gln Gly Thr Lys Lys
1               5                   10                  15

Lys Gly Val Leu Glu Met Trp Arg Gly Arg Thr His Ala Ser Lys Leu
            20                  25                  30

Pro Lys Pro Thr Gly Gly Phe Phe Arg Val Arg Thr Met Gly Lys Glu
        35                  40                  45

Ala Ser Gln Leu Pro His Glu Thr Asp Ala Arg Gly Thr Asp Pro Ile
    50                  55                  60

Ser Pro Ser Gly Pro Ser Ser Arg Asn Ala Arg Gly Val Tyr Ala Glu
65                  70                  75                  80

Gly Glu Lys Ser Glu Gly Ala Glu Gly Thr Leu Gln Arg Gly Asp
                85                  90                  95

Gly Gly Leu Ala Ala Pro Gln Phe Ser Leu Trp Lys Arg Pro Val Val
            100                 105                 110

Thr Ala Tyr Ile Glu Asp Gln Pro Val Gln Val Leu Leu Asp Thr Gly
        115                 120                 125

Ala Asp Asp Ser Ile Val Ala Gly Ile Glu Leu Gly Leu Asn Tyr Lys
    130                 135                 140

Pro
145

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggaggaggag atccggaagt                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agaacctgcc gttgcgagaa                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tccacagtga ccagtctcat                                               20

<210> SEQ ID NO 10
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 10
gatggcagtg acgcgtgtct                                                   20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgagtgcaga ggtggcagaa                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtgacgcgtg tctggaggtt                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcaggcacag attcaacaag                                                   20

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcaactgctg aatagccaag tc                                                22

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggctgggata gtgcagcaac agcaacag                                          28

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 16
aagcgggagg ggaagagaac actggcc                                          27

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgttggacgt ggtcaagaga caac                                             24

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gggaggggaa gagaacactg gcctata                                          27

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gagaagaaga cggtggagaa                                                  20

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggattgcgag tatccatctt cc                                               22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agaaggctag ccgcaagagg                                                  20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
taccttcacg tcccgctcag                                          20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gacacagcag ggactttcca                                          20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttcctccgtc gcggttggtt                                          20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
actcctgagt acggctgagt                                          20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caacaggtct tctgccaatc                                          20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggctgagtga aggcagtaag                                          20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tctgccaatc cgaatctgtc                                          20

```
<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tgggagatgg gcgcgagaaa ctccgtc                                         27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tccacatttc cagcagccct gtcttct                                         27

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agggaagaaa gcagatgaat tagaa                                           25

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcattttgaa tcagcagtgt ttgagtcatc ca                                   32

<210> SEQ ID NO 33
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
acgcacagca tccaag                                                     16

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttgagccat ggggaaattg                                                 20
```

-continued

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggagatggat tcagctagga                                              20

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggggcttctt tccccatgga cc                                           22

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggctgggata gtgcagcaac agcaacag                                     28

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gggaggggaa gagaacactg gcctata                                      27

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgttggacgt ggtcaagaga caac                                         24

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
aagcgggagg ggaagagaac actggcc                                      27

<210> SEQ ID NO 41
<211> LENGTH: 27

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgggagatgg gcgcgagaaa ctccgtc                                        27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tccacatttc cagcagccct gtcttct                                        27

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agggaagaaa gcagatgaat tagaa                                          25

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcattttgaa tcagcagtgt ttgagtcatc ca                                  32

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
aagaattgtt gcgattgaca gtct                                           24

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tgcacacccc catgaattta                                                20

<210> SEQ ID NO 47
<211> LENGTH: 29
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 47
actaaaaacc tccagacacg cgtcactgc                                         29
```